United States Patent [19]

Watanabe et al.

[11] Patent Number: 4,784,941

[45] Date of Patent: Nov. 15, 1988

[54] EXPRESSION AND DIAGNOSTIC USE OF PENV-3 ENCODED PEPTIDES WHICH ARE IMMUNOLOGICALLY REACTIVE WITH ANTIBODIES TO LAV

[75] Inventors: Susan M. Watanabe, Seattle; Wesley L. Cosand, Bothell; Susan McArdle; Bruce M. Travis, both of Seattle, all of Wash.

[73] Assignee: Genetic Systems Corporation, Seattle, Wash.

[21] Appl. No.: 783,299

[22] Filed: Oct. 2, 1985

Related U.S. Application Data

[63] Continuation-in-part of Ser. No. 721,237, Apr. 8, 1985.

[51] Int. Cl.$^4$ .................. G01N 33/545; G01N 33/53; C12Q 1/70

[52] U.S. Cl. .......................................... 435/5; 435/7; 435/70; 436/531; 436/811; 530/324; 530/325; 530/326; 530/327; 530/328; 530/329

[58] Field of Search ................. 435/5, 7; 436/53, 811; 530/324-329

[56] References Cited

U.S. PATENT DOCUMENTS

| | | | |
|---|---|---|---|
| 4,520,113 | 5/1985 | Gallo et al. | 436/504 |
| 4,525,300 | 6/1985 | Yoshida et al. | 260/112.5 R |
| 4,554,101 | 11/1985 | Hopp | 436/543 |
| 4,572,800 | 2/1986 | Shimizu et al. | 260/112.5 R |
| 4,629,783 | 12/1986 | Cosano | 530/324 |

OTHER PUBLICATIONS

Schupbach et al., Science, 224, (1984), 503.
Sarngadharan et al., Science, 224, (1984), 506.
Schupbach et al., N.E. J. Med., 312, (1985), 265.
Laurence et al., N.E. J. Med., 311, (1984), 1269.
Levy et al., Science, 2251, (1984), 840.
Kaminsky et al., PNAS, 82, (1985), 5535.
Kalyanaraman et al., Science, 225, (1985), 321.
Vilmer et al., Lancet, 1, (1984), 753.
Kitchen et al., Nature, 312, (1984), 367.
Wain-Hobson et al., Cell, 40, (1985), 9.
Muesing et al., Nature, 313, (1985), 450.
Allan et al., Science, 228, (1985), 1091.
Sanchez-Pescador et al., Science, 227, (1985), 484.
Crowl et al., Cell, 41, (1985), 979.
Chang et al., Science, 228, (1985), 93.
Chang et al., Biotechnology, 3, (1985), 905.
Veronese et al., Science, 229, (1985), 1402.

Primary Examiner—Christine M. Nucker

[57] ABSTRACT

A method of expressing peptides which are immunologically reactive with antibodies to LAV is disclosed. The peptides are produced by bacterial host cells transformed with a recombinant plasmid which includes appropriate procaryotic transcriptional and translational signals for expression, followed by a DNA sequence coding for a peptide comprising the amino acid sequence as shown in FIG. 5 starting with isoleucine, number 1, and ending with threonine, number 173. The peptides of the present invention are immunologically reactive with antibodies to LAV, or antibodies to viruses defined to be the same as or equivalent to LAV. The peptides produced by the method disclosed may be used to screen for the presence of antibodies to LAV in a biological fluid, to determine the presence of LAV antigen in a biological fluid, or within a method for producing antibodies to LAV through the immunization of an animal with the peptide. Further, the pNEV-3 encoded peptides may be used as a vaccine against infection by the causative virus for acquired immune deficiency syndrome.

17 Claims, 11 Drawing Sheets

ENV-3

Ile Phe Arg Pro Gly Gly Gly Asp Met Arg Asp Asn Trp Arg Ser Glu

Leu Try Lys Tyr Lys Val Val Lys Ile Glu Pro Leu Gly Val Ala Pro

Thr Lys Ala Lys Arg Arg Val Val Gln Arg Glu Lys Arg Ala Val Gly

Ile Gly Ala Leu Phe Leu Gly Phe Leu Gly Ala Ala Gly Ser Thr Met

Gly Ala Gly Ser Met Thr Leu Thr Val Gln Ala Arg Gln Leu Leu Ser

Gly Ile Val Gln Gln Gln Asn Asn Leu Leu Arg Ala Ile Glu Ala Gln

Gln His Leu Leu Gln Leu Thr Val Trp Gly Ile Lys Gln Leu Gln Ala

Arg Ile Leu Ala Val Glu Arg Tyr Leu Lys Asp Gln Gln Leu Leu Gly

Ile Trp Gly Cys Ser Gly Lys Leu Ile Cys Thr Thr Ala Val Pro Trp

Asn Ala Ser Trp Ser Asn Lys Ser Leu Glu Gln Ile Trp Asn Asn Met

Thr Trp Met Glu Trp Asp Arg Glu Ile Asn Asn Tyr Thr pJH11: 5' GAG ATC CCC GGG CGA GCT CGA ATT CGA GCT

┌─BamHI─┐
CGC CCG GGG ATC CTC TAG AGT CGA CCT GCA

┌─HindIII─┐
GCC CAA GCT T  3'

FIGURE 5

ENV-3

```
        #5
Ile Phe Arg Pro Gly Gly Gly Asp Met Arg Asp Asn Trp Arg Ser Glu

30
Leu Try Lys Tyr Lys Val Val Lys Ile Glu Pro Leu Gly Val Ala Pro

#2         40
Thr Lys Ala Lys Arg Arg Val Val Gln Arg Glu Lys Arg Ala Val Gly

50           #1                         60
Ile Gly Ala Leu Phe Leu Gly Phe Leu Gly Ala Ala Gly Ser Thr Met 70                                  80
Gly Ala Gly Ser Met Thr Leu Thr Val Gln Ala Arg Gln Leu Leu Ser

90
Gly Ile Val Gln Gln Gln Asn Asn Leu Leu Arg Ala Ile Glu Ala Gln 100                            110
Gln His Leu Leu Gln Leu Thr Val Trp Gly Ile Lys Gln Leu Gln Ala

120
Arg Ile Leu Ala Val Glu Arg Tyr Leu Lys Asp Gln Gln Leu Leu Gly

130             #3              140
Ile Trp Gly Cys Ser Gly Lys Leu Ile Cys Thr Thr Ala Val Pro Trp 150                                  160
Asn Ala Ser Trp Ser Asn Lys Ser Leu Glu Gln Ile Trp Asn Asn Met

170    #4
Thr Trp Met Glu Trp Asp Arg Glu Ile Asn Asn Tyr Thr
```

FIGURE 6A

Lys Glu Gln Lys Thr Val Ala Met Arg Val Lys Glu Lys Tyr Gln His
AAA GAG CAG AAG ACA GTG GCA ATG AGA GTG AAG GAG AAA TAT CAG CAC

Leu Trp Arg Trp Gly Trp Lys Trp Gly Thr Met Leu Leu Gly Ile Leu
TTG TGG AGA TGG GGG TGG AAA TGG GGC ACC ATG CTC CTT GGG ATA TTG
        5800

Met Ile Cys Ser Ala Thr Glu Lys Leu Trp Val Thr Val Tyr Tyr Gly
ATG ATC TGT AGT GCT ACA GAA AAA TTG TGG GTC ACA GTC TAT TAT GGG

Val Pro Val Trp Lys Glu Ala Thr Thr Thr Leu Phe Cys Ala Ser Asp
GTA CCT GTG TGG AAG GAA GCA ACC ACC ACT CTA TTT TGT GCA TCA GAT
            5900

Ala Lys Ala Tyr Asp Thr Glu Val His Asn Val Trp Ala Thr His Ala
GCT AAA GCA TAT GAT ACA GAG GTA CAT AAT GTT TGG GCC ACA CAT GCC

Cys Val Pro Thr Asp Pro Asn Pro Gln Glu Val Val Leu Val Asn Val
TGT GTA CCC ACA GAC CCC AAC CCA CAA GAA GTA GTA TTG GTA AAT GTG
                6000

Thr Glu Asn Phe Asn Met Trp Lys Asn Asp Met Val Glu Gln Met His
ACA GAA AAT TTT AAC ATG TGG AAA AAT GAC ATG GTA GAA CAG ATG CAT

Glu Asp Ile Ile Ser Leu Trp Asp Gln Ser Leu Lys Pro Cys Val Lys
GAG GAT ATA ATC AGT TTA TGG GAT CAA AGC CTA AAG CCA TGT GTA AAA
                    6100

Leu Thr Pro Leu Cys Val Ser Leu Lys Cys Thr Asp Leu Gly Asn Ala
TTA ACC CCA CTC TGT GTT AGT TTA AAG TGC ACT GAT TTG GGG AAT GCT

FIGURE 6B

```
Thr Asn Thr Asn Ser Ser Asn Thr Asn Ser Ser Ser Gly Glu Met Met
ACT AAT ACC AAT AGT AGT AAT ACC AAT AGT AGT AGC GGG GAA ATG ATG
                                6200

Met Glu Lys Gly Glu Ile Lys Asn Cys Ser Phe Asn Ile Ser Thr Ser
ATG GAG AAA GGA GAG ATA AAA AAC TGC TCT TTC AAT ATC AGC ACA AGC

Ile Arg Gly Lys Val Gln Lys Glu Tyr Ala Phe Phe Tyr Lys Leu Asp
ATA AGA GGT AAG GTG CAG AAA GAA TAT GCA TTT TTT TAT AAA CTT GAT

6300
Ile Ile Pro Ile Asp Asn Asp Thr Thr Ser Tyr Thr Leu Thr Ser Cys
ATA ATA CCA ATA GAT AAT GAT ACT ACC AGC TAT ACG TTG ACA AGT TGT

Asn Thr Ser Val Ile Thr Gln Ala Cys Pro Lys Val Ser Phe Glu Pro
AAC ACC TCA GTC ATT ACA CAG GCC TGT CCA AAG GTA TCC TTT GAG CCA
                                            6400

Ile Pro Ile His Tyr Cys Ala Pro Ala Gly Phe Ala Ile Leu Lys Cys
ATT CCC ATA CAT TAT TGT GCC CCG GCT GGT TTT GCG ATT CTA AAA TGT

Asn Asn Lys Thr Phe Asn Gly Thr Gly Pro Cys Thr Asn Val Ser Thr
AAT AAT AAG ACG TTC AAT GGA ACA GGA CCA TGT ACA AAT GTC AGC ACA
                                        6500

Val Gln Cys Thr His Gly Ile Arg Pro Val Val Ser Thr Gln Leu Leu
GTA CAA TGT ACA CAT GGA ATT AGG CCA GTA GTA TCA ACT CAA CTG CTG

Leu Asn Gly Ser Leu Ala Glu Glu Glu Val Val Ile Arg Ser Ala Asn
TTG AAT GGC AGT CTA GCA GAA GAA GAG GTA GTA ATT AGA TCT GCC AAT
                                                6600

Phe Thr Asp Asn Ala Lys Thr Ile Ile Val Gln Leu Asn Gln Ser Val
TTC ACA GAC AAT GCT AAA ACC ATA ATA GTA CAG CTG AAC CAA TCT GTA
```

FIGURE 6C

```
Glu Ile Asn Cys Thr Arg Pro Asn Asn Asn Thr Arg Lys Ser Ile Arg
GAA ATT AAT TGT ACA AGA CCC AAC AAC AAT ACA AGA AAA AGT ATC CGT
                                                          6700

Ile Gln Arg Gly Pro Gly Arg Ala Phe Val Thr Ile Gly Lys Ile Gly
ATC CAG AGG GGA CCA GGG AGA GCA TTT GTT ACA ATA GGA AAA ATA GGA

Asn Met Arg Gln Ala His Cys Asn Ile Ser Arg Ala Lys Trp Asn Ala
AAT ATG AGA CAA GCA CAT TGT AAC ATT AGT AGA GCA AAA TGG AAT GCC
                                                         6800

Thr Leu Lys Gln Ile Ala Ser Lys Leu Arg Glu Gln Phe Gly Asn Asn
ACT TTA AAA CAG ATA GCT AGC AAA TTA AGA GAA CAA TTT GGA AAT AAT

Lys Thr Ile Ile Phe Lys Gln Ser Ser Gly Gly Asp Pro Glu Ile Val
AAA ACA ATA ATC TTT AAG CAA TCC TCA GGA GGG GAC CCA GAA ATT GTA

Thr His Ser Phe Asn Cys Gly Gly Glu Phe Phe Tyr Cys Asn Ser Thr
ACG CAC AGT TTT AAT TGT GGA GGG GAA TTT TTC TAC TGT AAT TCA ACA
6900

Gln Leu Phe Asn Ser Thr Trp Phe Asn Ser Thr Trp Ser Thr Glu Gly
CAA CTG TTT AAT AGT ACT TGG TTT AAT AGT ACT TGG AGT ACT GAA GGG

Ser Asn Asn Thr Glu Gly Ser Asp Thr Ile Thr Leu Pro Cys Arg Ile
TCA AAT AAC ACT GAA GGA AGT GAC ACA ATC ACA CTC CCA TGC AGA ATA
     7000

Lys Gln Phe Ile Asn Met Trp Gln Glu Val Gly Lys Ala Met Tyr Ala
AAA CAA TTT ATA AAC ATG TGG CAG GAA GTA GGA AAA GCA ATG TAT GCC

Pro Pro Ile Ser Gly Gln Ile Arg Cys Ser Ser Asn Ile Thr Gly Leu
CCT CCC ATC AGC GGA CAA ATT AGA TGT TCA TCA AAT ATT ACA GGG CTG
          7100
```

FIGURE 6D

```
Leu Leu Thr Arg Asp Gly Gly Asn Asn Asn Asn Gly Ser Glu Ile Phe
CTA TTA ACA AGA GAT GGT GGT AAT AAC AAC AAT GGG TCC GAG ATC TTC

Arg Pro Gly Gly Gly Asp Met Arg Asp Asn Trp Arg Ser Glu Leu Tyr
AGA CCT GGA GGA GGA GAT ATG AGG GAC AAT TGG AGA AGT GAA TTA TAT
                7200

Lys Tyr Lys Val Val Lys Ile Glu Pro Leu Gly Val Ala Pro Thr Lys
AAA TAT AAA GTA GTA AAA ATT GAA CCA TTA GGA GTA GCA CCC ACC AAG

Ala Lys Arg Arg Val Val Gln Arg Glu Lys Arg Ala Val Gly Ile Gly
GCA AAG AGA AGA GTG GTG CAG AGA GAA AAA AGA GCA GTG GGA ATA GGA
                    7300

Ala Leu Phe Leu Gly Phe Leu Gly Ala Ala Gly Ser Thr Met Gly Ala
GCT TTG TTC CTT GGG TTC TTG GGA GCA GCA GGA AGC ACT ATG GGC GCA

Arg Ser Met Thr Leu Thr Val Gln Ala Arg Gln Leu Leu Ser Gly Ile
CGG TCA ATG ACG CTG ACG GTA CAG GCC AGA CAA TTA TTG TCT GGG ATA
                    7400

Val Gln Gln Gln Asn Asn Leu Leu Arg Ala Ile Glu Ala Gln Gln His
GTG CAG CAG CAG AAC AAT TTG CTG AGG GCT ATT GAG GCG CAA CAG CAT

Leu Leu Gln Leu Thr Val Trp Gly Ile Lys Gln Leu Gln Ala Arg Ile
CTG TTG CAA CTC ACA GTC TGG GGC ATC AAG CAG CTG CAG GCA AGA ATC
                        7500

Leu Ala Val Glu Arg Tyr Leu Lys Asp Gln Gln Leu Leu Gly Ile Trp
CTG GCT GTG GAA AGA TAC CTA AAG GAT CAA CAG CTC CTG GGG ATT TGG

Gly Cys Ser Gly Lys Leu Ile Cys Thr Thr Ala Val Pro Trp Asn Ala
GGT TGC TCT GGA AAA CTC ATT TGC ACC ACT GCT GTG CCT TGG AAT GCT
                    7600
```

FIGURE 6E

```
Ser Trp Ser Asn Lys Ser Leu Glu Gln Ile Trp Asn Asn Met Thr Trp
AGT TGG AGT AAT AAA TCT CTG GAA CAG ATT TGG AAT AAC ATG ACC TGG

Met Glu Trp Asp Arg Glu Ile Asn Asn Tyr Thr Ser Leu Ile His Ser
ATG GAG TGG GAC AGA GAA ATT AAC AAT TAC ACA AGC TTA ATA CAT TCC
                                                7700

Leu Ile Glu Glu Ser Gln Asn Gln Gln Glu Lys Asn Glu Gln Glu Leu
TTA ATT GAA GAA TCG CAA AAC CAG CAA GAA AAG AAT GAA CAA GAA TTA

Leu Glu Leu Asp Lys Trp Ala Ser Leu Trp Asn Trp Phe Asn Ile Thr
TTG GAA TTA GAT AAA TGG GCA AGT TTG TGG AAT TGG TTT AAC ATA ACA
                                                7800

Asn Trp Leu Trp Tyr Ile Lys Ile Phe Ile Met Ile Val Gly Gly Leu
AAT TGG CTG TGG TAT ATA AAA ATA TTC ATA ATG ATA GTA GGA GGC TTG

Val Gly Leu Arg Ile Val Phe Ala Val Leu Ser Ile Val Asn Arg Val
GTA GGT TTA AGA ATA GTT TTT GCT GTA CTT TCT ATA GTG AAT AGA GTT
                                                7900

Arg Gln Gly Tyr Ser Pro Leu Ser Phe Gln Thr His Leu Pro Thr Pro
AGG CAG GGA TAT TCA CCA TTA TCG TTT CAG ACC CAC CTC CCA ACC CCG

Arg Gly Pro Asp Arg Pro Glu Gly Ile Glu Glu Glu Gly Gly Glu Arg
AGG GGA CCC GAC AGG CCC GAA GGA ATA GAA GAA GAA GGT GGA GAG AGA
                                                8000

Asp Arg Asp Arg Ser Ile Arg Leu Val Asn Gly Ser Leu Ala Leu Ile
GAG AGA GAG AGA TCC ATT CGA TTA GTG AAC GGA TCC TTA GCA CTT ATC

Trp Asp Asp Leu Arg Ser Leu Cys Leu Phe Ser Tyr His Arg Leu Arg
TGG GAC GAT CTG CGG AGC CTG TGC CTC TTC AGC TAC CAC CGC TTG AGA

Asp Leu Leu Leu Ile Val Thr Arg Ile Val Glu Leu Leu Gly Arg Arg
GAC TTA CTC TTG ATT GTA ACG AGG ATT GTG GAA CTT CTG GGA CGC AGG
8100
```

FIGURE 6F

```
Gly Trp Glu Ala Leu Lys Tyr Trp Trp Asn Leu Leu Gln Tyr Trp Ser
GGG TGG GAA GCC CTC AAA TAT TGG TGG AAT CTC CTA CAG TAT TGG AGT

Gln Glu Leu Lys Asn Ser Ala Val Ser Leu Leu Asn Ala Thr Ala Ile
CAG GAA CTA AAG AAT AGT GCT GTT AGC TTG CTC AAT GCC ACA GGC ATA
         8200

Ala Val Ala Glu Gly Thr Asp Arg Val Ile Glu Val Val Gln Gly Ala
GCA GTA GCT GAG GGG ACA GAT AGG GTT ATA GAA GTA GTA CAA GGA GCT

Cys Arg Ala Ile Arg His Ile Pro Arg Arg Ile Arg Gln Gly Leu Glu
TGT AGA GCT ATT CGC CAC ATA CCT AGA AGA ATA AGA CAG GGC TTG GAA
             8300

Arg Ile Leu Leu
AGG ATT TTG CTA TAA
```

EXPRESSION AND DIAGNOSTIC USE OF PENV-3 ENCODED PEPTIDES WHICH ARE IMMUNOLOGICALLY REACTIVE WITH ANTIBODIES TO LAV

CROSS-REFERENCE TO RELATED APPLICATION

This application is a continuation-in-part of appliction Ser. No. 721,237 filed Apr. 8, 1985, which application is pending.

DESCRIPTION

1. Technical Field

The present invention relates in general to the expression of viral proteins through the use of recombinant DNA technology, and more specifically, to the expression of proteins which are immunologically reactive with antibodies to lymphadenopathy-associated virus (LAV).

2. Background Art

Acquired immune deficiency syndrome (AIDS) is a transmissible deficiency of cellular immunity characterized by opportunistic infections and certain rare malignancies. The dominant risk groups for AIDS include homosexually active males, intravenous drug abusers, recipients of transfusions and blood products, and the heterosexual partners and children of high-risk individuals, suggesting the involvement of an infectious agent transmitted through initmate contact or blood products.

Recent evidence indicates that the infectious agent responsible for disease transmission is a novel lymphotropic retrovirus, known as lymphadenopathy-associated virus (Barré-Sinoussi et al., *Science* 220: 868 (1983)). Similar viruses have been reported by other scientific groups (Popovic et al., *Science* 224: 497 (1984); Levy et al., *Science* 225: 840 (1984); Vilmer et al., *Lancet* 1: 753 (1983)) and designated human T-cell lymphotropic virus type III (HTLV-III), AIDS-associated retrovirus (ARV), or immune deficiency-associated virus (IDAV). Still more recent data indicates that LAV, HTLV-III, ARV, and IDAV share several important characteristics, including substantial nucleotide homology (Wain-Hobson et al., *Cell* 40: 9 (1985); Muesing et al., *Nature* 313: 450 (1985); Sanchez-Pescador et al., *Science* 227: 484 (1985)), and should be considered isolates of the same virus, although there is a likelihood that strain-to-strain variations among the viral isolates will exist. In addition to exhibiting substantial nucleotide homology, the isolates are similar with respect to morphology, cytopathology, requirements for optimum reverse transcriptase activity, and at least some antigenic properties (Levy, supra; Schupbach et al., *Science* 224: 503 (1984)).

As noted above, the virus is known to be transmissable through blood products (blood, blood serum, blood plasma, and fractions thereof), making it important to screen the blood products to determine if the donor has been exposed to the virus. This can be done in any of several ways, including enzyme-linked immunosorbent assay (ELISA) for the detection of antibodies to LAV and related viruses. Individuals whose blood contains antibodies to LAV are said to be "seropositive." Blood from seropositive donors may be eliminated from the blood supply upon detection, thereby helping to prevent the spread of the disease.

The immune response of individuals exposed to LAV is variable. Antibodies can be produced to any of several viral proteins, including p13, p18, p25, p36, gp43, p55, gp65, gp110, etc. (Schupbach et al., *New Engl. J. Med.* 312: 265 (1985)). It is also likely that not all individuals will make antibodies to the same proteins or to the same epitope on a given protein.

The detection of seropositive individuals, as currently practiced, has several inherent problems. Foremost among these problems is the need to isolate antigen from whole viruses for the immunological assays. This isolation requires the manipulation of large volumes of live, potentially infectious virus, and as such poses a significant safety hazard. In addition, there are concerns relating to the yield, purity, and reproducibility of virus from one preparation to another. This may result in an unacceptable number of false positives and/or negatives. Consequently, there is a need in the art for alternative methods of producing viral antigens which are useful in blood screening assays and which further provide other related advantages.

DISCLOSURE OF INVENTION

Briefly stated, the present invention discloses a peptide which is immunologically reactive with antibodies to LAV, the peptide comprising the amino acid sequence of FIG. 5, starting with isoleucine, number 1, and ending with threonine, number 173. A recombinant plasmid capable of replication in bacterial host cells is also disclosed. The plasmid includes procaryotic transciptional and translational signals for expression, followed by a DNA sequence coding for a peptide comprising the amino acid sequence described above. In a preferred embodiment, signals are chosen from an operon, such as the trp operon, which is inducible and/or suppressible. Bacterial cells, such as *E. coli*, which have been transformed with the recombinant plasmid described above, are also disclosed.

Another aspect of the invention discloses a method for preparing proteins which are immunologically reactive with antibodies to LAV. The method comprises introducing a recombinant plasmid capable of replication into bacterial host cells. The plasmid includes procaryotic transciptional and translational signals for expression, followed by a DNA sequence coding for a peptide comprising the amino acid sequence of FIG. 5, starting with isoleucine, number 1, and ending with threonine, number 173, said peptide being immunologically reactive with antibodies to LAV. Subsequent to the introduction of the plasmid, the bacterial host is grown in an appropriate medium. Expression of the protein may then be induced and the protein product of the sequence isolated from the bacterial host. The protein product may be purified subsequent to isolation, for example, by gel permeation chromatography.

A further aspect of the invention discloses a method for determining the presence of antibodies to LAV in a biological fluid. In one embodiment, the method comprises incubating the biological fluid with a protein produced by bacterial cells transformed with a recombinant plasmid as described above, thereby forming a reaction mixture, and subsequently analyzing the reaction mixture to determine the presence of the antibodies. In a preferred embodiment, the step of analyzing the reaction mixture comprises contacting the reaction mixture with a labeled specific binding partner for the antibody. In another embodiment, the presence of antibodies to LAV is determined by carrying out a competition between a sample suspected of containing antibody and a labeled monoclonal antibody for binding to an immobilized recombinant protein. The reaction mixture is subsequently analyzed to determine the amount of labeled antibody bound to the solid phase.

Yet another aspect of the invention discloses a method for determining the presence of LAV antigen in a biological fluid, comprising incubating the biological fluid, either sequentially or simultaneously, with a labeled protein produced by bacterial cells transformed with a recombinant plasmid as described above, and an antibody to the protein such that specific binding occurs. Subsequently, the reaction mixture formed during the incubation is analyzed to determine the amount of label associated with the antibody.

A method for producing antibodies to LAV comprising immunizing an animal with a protein produced by bacterial cells transformed with a recombinant plasmid as described above is also disclosed.

An additional aspect of the present invention discloses a method for determining the presence of antibodies to LAV in a biological fluid, comprising conjugating latex beads to a protein produced by bacterial cells transformed with a recombinant plasmid capable of replication in bacterial host cells, the plasmid including procaryotic transcriptional and translational signals for expression. The signals are followed by a DNA sequence coding for a peptide comprising the amino acid sequence of FIG. 5, starting with isoleucine, number 1, and ending with threonine, number 173, the peptide being immunologically reactive with antobodies to LAV. Subsequently, the biological fluid is incubated with the bead/protein conjugate, thereby forming a reaction mixture. The reaction mixture is then analyzed to determine the presence of the antibodies.

The proteins produced within the present invention, when used with a suitable carrier or diluent, form an immunologically effective vaccine composition. By administering to an individual an immunogenically effective amount of a protein encoded by a DNA sequence comprising the amino acid sequence of FIG. 5, starting with isoleucine, number 1, and ending with threonine, number 173, attached to a physiologically acceptable carrier, infection caused by the virus responsible for AIDS can be prevented.

Other aspects of the invention will become evident upon reference to the following detailed description and attached drawings.

BRIEF DESCRIPTION OF THE DRAWINGS

FIG. 5 illustrates the amino acid sequence of ENV-3.

FIG. 6 illustrates the nucleotide sequence of the env region and its protein product.

BEST MODE FOR CARRYING OUT THE INVENTION

Figure 1:
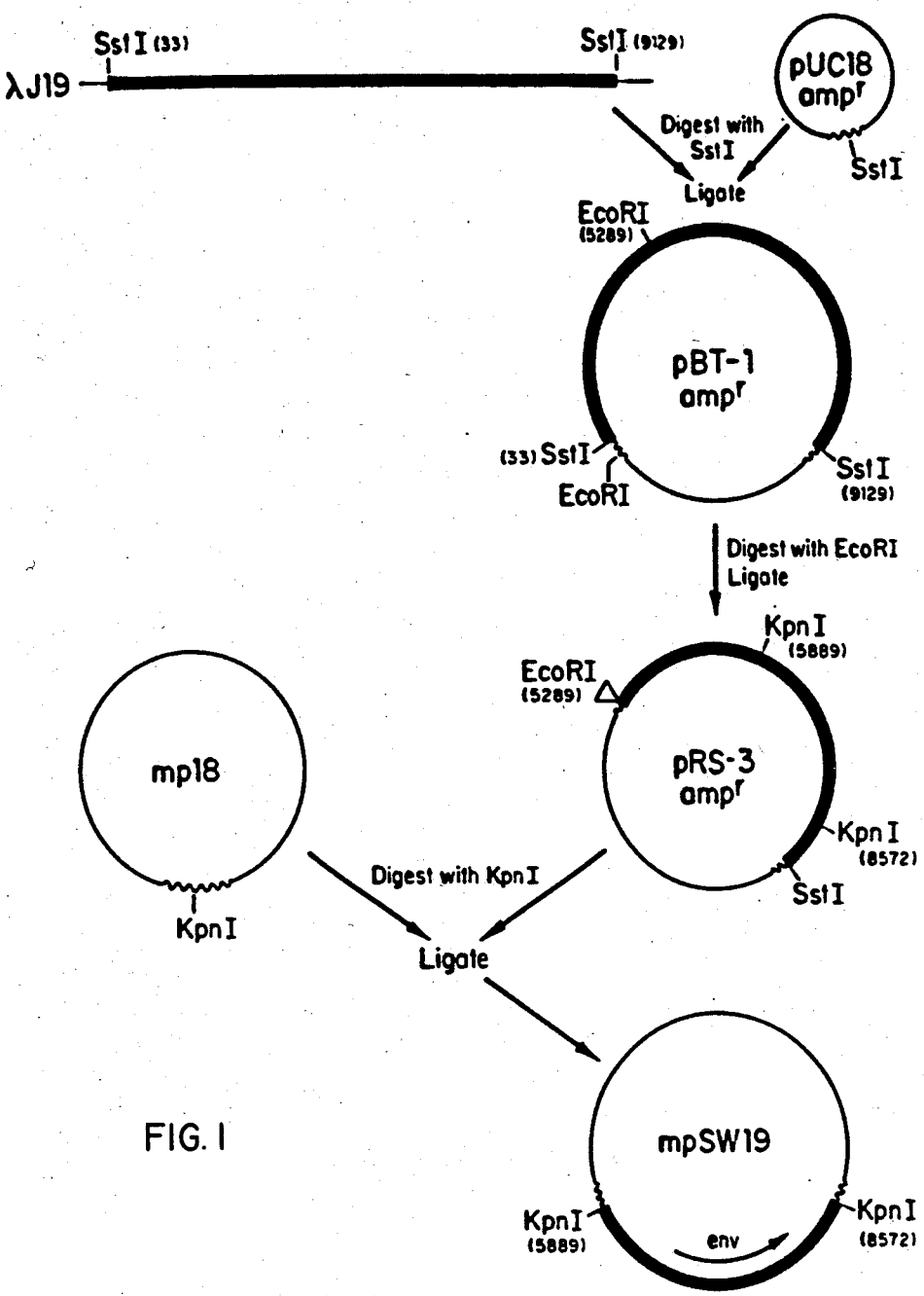
FIG. 1 illustrates the construction of mpSW19 from λJ19.

Prior to setting forth the invention, it may be helpful to an understanding thereof to set forth definitions of certain terms to be used hereinafter.

Lymphadenopathy-Associated Virus (LAV):

A human T-lymphotropic retrovirus. For purposes of the present invention, a virus is considered to be the same as or equivalent to LAV if it substantially fulfills the following criteria:

(a) the virus is tropic for T-lymphocytes, especially T-helper cells (CD4+, according to the international nomenclature defined in Bernard et al., eds., *Leucocyte Typing,* New York: Springer Verlag (1984));

(b) the virus is cytopathic for infected CD4+ cells (rather than transforming, as are HTLV-I and II);

(c) the virus encodes an RNA-dependent DNA polymerase (reverse transcriptase) which is $Mg^{2+}$-dependent (optimum concentration 5 mM, optimum pH 7.8), not inhibitable by actinomycin D and can employ oligo $(dT)_{12-18}$ as a primer for reverse transcription from its 3' LTR;

(d) the virus bands in a sucrose gradient at a density of approximately 1.16;

(e) the virus can be labeled with [$^3$H] uridine;

(f) the virus is distinct by immunological and nucleotide sequence criteria from members of the HTLV-I/II family of viruses (by this criterion HTLV-III is not to be considered a member of the HTLV-I/II family);

(g) the virus is substantially cross-reactive immunologically with the proteins encoded by the gag and env regions of LAV; and (h) the virus shares substantial nucleotide homology (75-100%) and amino acid seqence homology (75-100%) with LAV.

Immunologically Reactive:

An antigen and an antibody are said to be "immunologically reactive" if they are capable of binding specifically to each other, typically with an affinity of at least $10^6 M^{-1}$, more often at least $10^8 M^{-1}$.

Transformed or Transformation:

The process of stably and heritably altering the genotype of a recipient cell or microorganism by the introduction of DNA.

Lymphadenopathy-associated virus (LAV) can be isolated from patients with AIDS or lymphadenopathy syndrome. The lymph nodes of such patients are typically biopsied and placed in culture medium supplemented as necessary to support growth. A mitogen such as interleukin-2 (IL-2) or phytohemagglutinin (PHA) can be included; anti-serum to human interferon can also be included. Reverse transcriptase activity typically appears about day 15 of culture, indicating the presence of virus. The virus can be concentrated from the culture supernatant using a non-ionic detergent, followed by banding in a sucrose gradient. These and other methods of purification are well known in the art and are described, for example, in Montelaro et al., *J. Virol.* 42: 1029 (1982).

LAV can be propagated in any of a number of ways. It can be cultured in T-lymphocytes derived from umbilical cord or peripheral blood or from bone marrow. Alternatively, it can be propagated in immortalized T-cells or B-cells; see, for example, Popovic et al., *Science* 224: 497 (1984), and Montagnier et al., *Science* 225: 63 (1984). Growth of the virus is usually monitored by the presence of reverse transcriptase activity.

A genomic clone of LAV can be prepared by any of several methods well known in the art, including but not limited to those described by Hahn et al., *Nature* 312: 166 (1984); Alizon et al., *Nature* 312: 757 (1984); Luciw et al., *Nature* 312: 760 (1984); and Muesing et al., *Nature* 313: 450 (1985).

Briefly, in one of these methods (Alizon et al.) DNA is isolated from LAV-infected T-cells of a healthy donor, partially digested with a restriction endonuclease such as Hind III, and the resultant digest fractionated electrophoretically. Fragments which correspond in size to the size of the entire LAV genome (approximately 9.2 Kb) are eluted from the gel, precipitated, resuspended, and ligated into the arms of an appropriately restricted vector. The ligation mix is packaged into bacteriophage particles. Bacteria are transformed with the bacteriophage, and the clones are screened in situ for LAV inserts using a suitable probe (such as a cDNA made from LAV-RNA). From such a clone, the desired region of LAV can be subcloned into a bacterial plasmid vector, such as pUC 18. Further subcloning may be desirable to remove unwanted sequences and to add additional restriction sites (in the form of a polylinker) at either end for the purpose of facilitating cloning into an expression vector.

The LAV sequences can then be subcloned into an inducible expression vector. A variety of expression vectors are known in the art and include λgt 11:Tn5 (Hall et al., Nature 311: 379 (1984)); trp E (Paul et al., Eur. J. Cell. Biol. 31: 171 (1983)); pINIII (Masui et al., Biotechnology, January 1984, p. 81).

The resultant proteins can be partially purified and used for a variety of purposes, including utilization as immunogens and antigens in immunoassays. For use as immunogens, the proteins can be injected into an animal, such as a mouse, rabbit, goat, etc., either in buffered solution or in adjuvant. Alternatively, the proteins can be purified by polyacrylamide gel electrophoresis and the bands of interest excised from the gel, triturated, and resuspended in buffer for injection into the host animal. Polyclonal or monoclonal antibodies can be prepared. For use as antigens in immunoassays, the proteins can be employed in labeled or unlabeled form. When the proteins are labeled, the lables can include radioisotopes, fluorophores, enzymes, luminescers, or particles. These and other labels are well known in the art and are described, for example, in the following U.S. Pat. Nos.: 3,766,162; 3,791,932; 3,817,837; 3,996,345; and 4,233,402.

Assays employing the recombinant proteins of the instant invention can be heterogeneous (i.e., requiring a separation step) or homogeneous. If the assay is heterogeneous, a variety of separation means can be employed, including centrifugation, filtration, chromatography, or magnetism.

One preferred assay for the screening of blood products or other physiological fluids for the presence of antibodies is by an ELISA. Typically, antigen is adsorbed to the surface of a microtiter well. Residual protein-binding sites on the surface are then blocked with an appropriate agent, such as bovine serum albumin (BSA), heat-inactivated normal goat serum (NGS), or BLOTTO, (a buffered solution of nonfat dry milk which also contains a preservative, salts, and an antifoaming agent). The well is then incubated with a sample suspected of containing specific antibody. The sample can be applied neat, or, more often, it can be diluted, usually in a buffered solution which contains a small amount (0.1–5.0% by weight) of protein, such as BSA, NGS, or BLOTTO. After incubating for a sufficient length of time to allow specific binding to occur, the well is washed to remove unbound protein and then incubated with a labeled, anti-human immunoglobulin antibody (αHuIg). The label can be chosen from a variety of enzymes, including horseradish peroxidase (HRP), β-galactosidase, alkaline phosphatase, and glucose oxidase. Sufficient time is allowed for specific binding to occur, then the well is again washed to remove unbound conjugate, and the substrate for the enzyme is added. Color is allowed to develop and the optical density of the contents of the well is determined visually or instrumentally.

For convenience, reagents for an ELISA may be provided in the form of kits. These kits can include microtiter plates to which viral proteins made by recombinant techniques have been pre-adsorbed, various diluents and buffers, labeled conjugates for the detection of specifically bound antibodies, and other signal-generating reagents, such as enzyme substrates, cofactors, and chromogens.

Due to the fact that a significant number of AIDS patients are highly immunosuppressed and have progressively lost the ability to make high-titer antibodies, the present invention utilizes a portion of the envelope (env) region of the LAV genome which codes for a protein which is immunologically reactive with antibodies to LAV. The presence of antibodies to the envelope glycoprotein of LAV is a better indicator of LAV infection that is the presence of antibodies to other viral proteins, because the antibody titers to the envelope glycoprotein are thought to persist during the later stages of the disease, while antibody to other proteins, such as the core proteins, may decline to less than detectable levels.

Another application of the recombinant proteins of this invention is use as human vaccines. The recombinant proteins can be extensively purified and formulated in a convenient manner, generally in concentrations of 1 μg to 20 mg per kg of host. Physiologically acceptable carriers, such as sterile water, saline, buffered saline, etc., can be employed. Adjuvants, such as aluminum hydroxide, can also be employed. Adjuvants, such as aluminum hydroxide, can also be employed. The vaccine can be administered by intravenous, subcutaneous, intramuscular, or peritoneal injection. One injection can be sufficient, but more often, multiple injections at weekly to monthly intervals are preferred.

Alternatively, vaccinia virus recombinants can be constructed which express regions of the LAV genome. For example, the constructs of this invention can be inserted into a plasmid such as pMM34 (Mackett, et al., Science 227: 433, 1985) and vaccinia virus hybrids containing the resultant chimeric plasmic, formed by homologous recombination. Immunization with such recombinant virus vaccines has been shown to be effective in eliciting protective immunity in animals to hepatitis B virus and vesicular stomatitis virus (Smith et al., Nature 311: 578, 1984).

The use of a recombinant protein vaccine in this manner eliminates the need to compose vaccines from inactivated preparations or avirulent strains of pathogenic microorganisms.

The genetic organization of LAV, 5'LTR-gag-pol-Q-env-F-3'-LTR, is unique among retroviruses. In all other known replication-competent retroviruses, the pol and env genes overlap; in LAV, they are separated by an open reading frame Q (Wain-Hobson et al., Cell 40: 9 (1985)).

The env open reading frame has a possible initiation site (methionine codon) at the eighth triplet and hence is expected to code for a protein of molecular weight 97 kd. This is consistent with the apparent molecular weight (110 kd) of the LAV glycoprotein on denaturing polyacrylamide gels. There are 32 potential N-glycosylation sites in the env gene (Asn-x-Ser/Thr). There are also three hydrophobic regions, characteristic of retroviral envelope proteins, corresponding to a signal peptide (encoded by nucleotides 5815-5850), a second region (7315-7350), and a transmembrane segment (7831-7896). The second region is preceded by an Arg/Lys-rich region which is thought to represent a proteolytic processing site (Wain-Hobson, supra).

As noted above, antibodies to the LAV glycoprotein (the env gene product) appear early in the course of virus infection and persist in the later stages of disease as well (Kitchen et al., Nature 312: 367 (1984)). Antibodies to the glycoprotein are, therefore, a particularly good indicator of prior exposure to LAV, making the glycoprotein, or portions thereof, particularly useful in blood screening assays.

Figure 3:
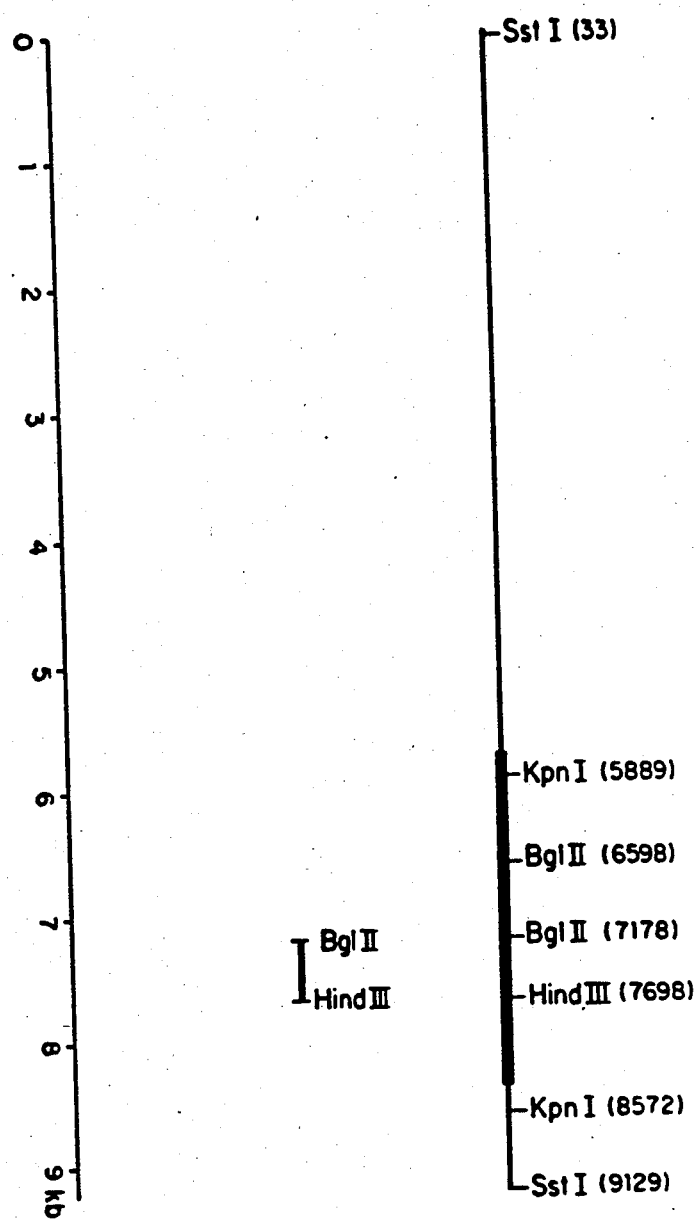
FIG. 3 illustrates the origin of the LAV insert in pENV-3.
Figure 4:
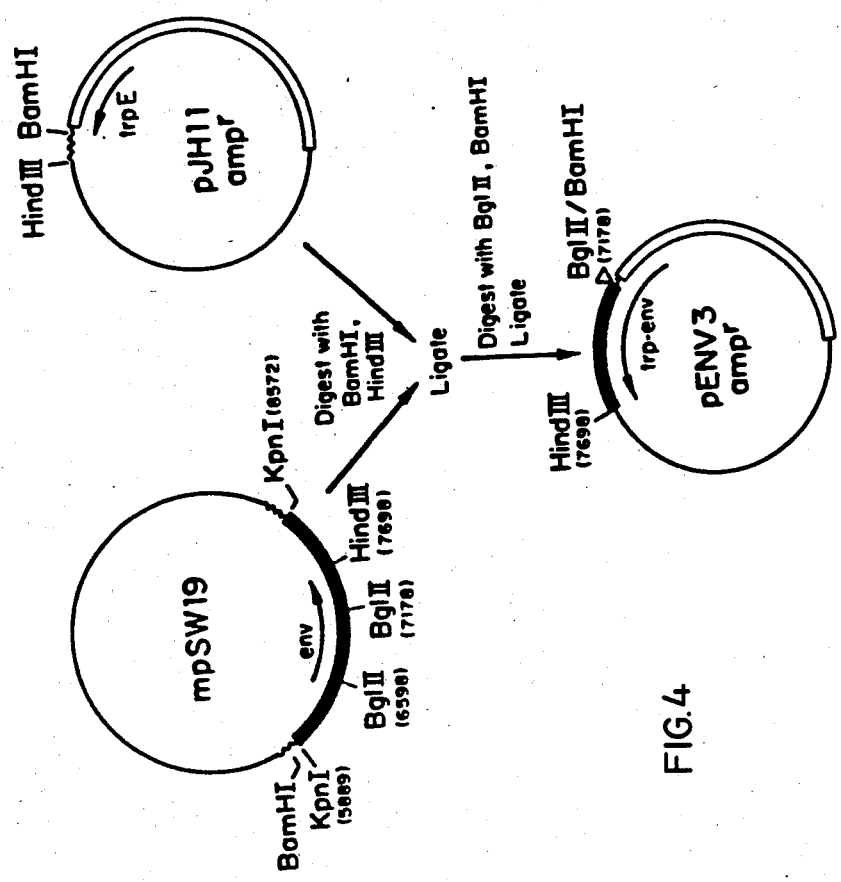
FIG. 4 illustrates the construction of pENV-3 from pJH 11 and mpSW19.

A particularly preferred portion of the env region of the LAV genome is ENV-3. As shown in FIGS. 3 and 4, ENV-3 spans the nucleotide sequence from bp 7178 to bp 7698. Referring now to FIG. 5, included within the region are the following sub-regions (overlined in FIG. 5): (1) a hydrophobic peptide encoded by bp 7315 through 7350; (2) a dodecapeptide containing putative proteolytic progressing sites for cleavage of the envelope precursor protein to gp 65 and gp 43; (3) a highly conserved region around two cysteine residues; (4) a conserved sequence at the 3' (carboxy) terminus; and (5) a conserved sequence at the 5' (amino) terminus.

Data obtained using synthetic peptides which correspond to the different sub-regions of ENV-3 indicate that the most important regions are those encompassing or in close proximity to the cysteine residues and those encompassing or in close proximity to the proteolytic processing region. The synthesis and screening of certain of these peptides are described in co-pending U.S. patent application Ser. No. 721,237, filed Apr. 8, 1985 by Watanabe, the text of which is hereby incorporated by reference.

Additionally, ENV-3 is almost totally devoid of potential glycosylation sites; hence the antigenicity of the recombinant protein can be reasonably expected to mimic that of the native protein. The entire sequence of the env gene and its protein product is shown in FIG. 6, in which the potential glycosylation sites are overlined. Referring to FIG. 6, it can be seen that a large stretch of ENV-3 is devoid of such sites, and that in comparison to the remainder of the gene, ENV-3 as a whole is strikingly underglycosylated.

In the following example, an LAV genomic clone designated λJ19 was subcloned into the bacterial plasmid vector, pUC 18. The resultant subclone, designated pBT-1 (assigned ATCC Accession Number 53069), was further subcloned to yield pRS-3, which contained predominantly env, F, and LTR region sequences. The env and part of the F sequences were further subcloned into M13mp18, and then regions of the env sequence were transferred into the trp E inducible expression vector. The env DNA was inserted in-frame downstream of the trp E gene, resulting in the expression of a trp E-env fusion protein when E. coli were tranformed with this construct. The resultant protein was partially purified and characterized by its reactivity in ELISA with sera from known seropositive and known seronegative individuals.

The following example is offered by way of illustration, and not by way of limitation.

EXAMPLE

A. Construction of the trp-env expression vectors

Any of several bacterial expression systems can be used to express foreign proteins. The trp E system was chosen for the expression LAV env sequences because it contains a strong inducible promoter and because its expression can also be suppressed so that foreign (and potentially toxic) protein does not accumulate within the bacteria for long periods of time.

Since there is no rapid and convenient way to screen or select for bacteria transformed with vector containing a foreign insert (as opposed to bacteria transformed with vector alone), it is convenient to subclone the desired region of a large piece of DNA (such as phage DNA) into a vector containing a selection system for inserts before transferring it to the trp E expression vector. This facilitates the screening of transformed bacteria for ones containing the desired insert.

The approach of applicants was, therefore, to first subclone in two steps most of the env region of the LAV genome into a transfer vector, M13mp18 (FIG. 1). Then, the Bam HI-Hind III fragment of this subclone was ligated into trp expression vector pJH 11. DNA from the resulting subclone was further modified to produce the desired product, pENV-3.

1. Subcloning LAV genome a. Preparation of phage DNA

The entire LAV genome was obtained from the Pasteur Institut in the form of λphage particles containing a 9.2 Kb genomic DNA insert in the Hind III site of phage λL47.1. This clone is referred to as λJ19 and is described in Wain-Hobson et al., Cell 40: 9 (1985). λJ19 phage particles were transfected into the Q359 strain of E. coli K-12 (the genotype of Q359 is hsdRk$^-$, hsdMk$^+$, supF, $\phi$80, P2) according to the procedure of Maniatis et al., Molecular Cloning: A Laboratory Manual, New York: Cold Spring Harbor Laboratory, 1982, at p. 64. A single plaque was picked and the phage amplified by the plate lysate method (Maniatis, supra, at p. 65). After a nine-hour incubation at 37° C., the plates (100 mm diameter) containing confluent plaques were overlaid with 5 ml of 100 mM NaCl/20 mM MgSO$_4$/50 mM Tris, pH 7.5. After incubating for twelve hours at 4° C., the liquid was collected and extracted two times with an equal volume of chloroform.

To 10 ml of the resultant aqueous phase containing phage particles was added 2 ml 0.25M EDTA/2.5% SDS/0.5M Tris, pH 9, and the suspension was incubated at 70° C. for fifteen minutes to disrupt the phage. 2.5 ml 8M potassium acetate was added, and the solution was incubated on ice for fifteen minutes, then centrifuged for ten minutes at 12,000×g at 4° C. to pellet protein. The supernatant was transferred to a 50 ml polypropylene centrifuge tube and extracted with an equal volume of phenol (pH 8, equilibrated with 1M Tris, pH 8) at 20° C. The aqueous phase was then extracted with an equal volume of chloroform:isoamylalcohol (24:1) at 20° C. To the aqueous phase was then added 2.5 volumes of 95% ethanol to precipitate the DNA. After centrifugation, the DNA pellet was dried and resuspended in 10 mM Tris HCl, pH 7.4/1 mM EDTA.

b. Subcloning the env region

Approximately 12 μg of λJ19 DNA prepared in A.1.a above was digested to completion with the restriction enzyme Sst I (Bethesda Research Labs, Bethesda, MD), which only cuts in the LTR regions of this isolate of LAV. The digest mixture was electrophoresed at 1 V/cm through 0.9% agarose in 0.089M Tris-borate/0.089M boric acid/1 mM EDTA. The position of the 9.1 Kb fragment was determined relative to molecular weight standards after staining with ethidium bromide. This band was electroeluted into NA45 paper (Schleicher and Schuell, Keene, NH). The DNA was recovered from the paper according to instructions provided by the manufacturer.

The 9.1 Kb Sst I fragment was ligated into the Sst I digested vector pUC 18, at a ratio of 10 insert molecules:1 vecor molecule. *E. coli* strain HB101 was transformed with the ligation mix by the CaCl$_2$ procedure of Maniatis, et al. (supra) and plated onto LB plus ampicillin (200 μg/ml) agar plates.

Single colonies were picked and diluted into 3 ml LB plus ampicillin medium and grown overnight at 37° C. with constant shaking. Plasmid DNA was prepared by the alkaline lysis method (Maniatis et al., supra, at p. 368). One colony was selected which contained the 9.1 Kb Sst I insert in an orientation such that the Eco RI site in the polylinker was closest to the 5' end of the LAV genome, as determined by restriction analysis of the plasmid DNA. This subclone was designated pBT-1 (FIG. 1).

Plasmid pBT-1 was then digested with Eco RI, and the vector, still containing the 3' end of the LAV genome, was religated. This served to remove the 5' Eco RI fragments from the plasmid. HB101 cells were transformed with the ligation mixture, and a colony containing the insert pRS-3 was identified by restriction analysis of the purified plasmid DNA.

The sequence between the Kpn I sites at bp 5889 and bp 8572 [numbering according to Wain-Hobson et al., *Cell* 40: 9 (1985)], containing most of the env region, was then transferred from pRS-3 to the M13mp18 vector. This was done to further remove extraneous (non-env) sequences and also to place the env sequences in a vector which utilizes β-galactosidase rather than ampicillin as the selectable/screenable marker. This was advantageous because the trp E expression vector uses ampicillin resistance as its selectable marker; transfer of an insert from one vector (pUC 18) encoding the ampicillin resistance factor to another (trp expression vector pJH 11) would make screening for the desired insert plus vector more difficult. M13 phage were screened by usingthe chromogenic substrate 5-bromo-4-chloro-3-indolyl-β-galactoside (Sigma Chemical Co.) to score for inactivation of β-galactosidase due to insertion of env sequence. Those phage containing inserts were screened for the orientation of the insert relative to restriction sites in the polylinker region. DNA was isolated from recombinant mpSW19, which has the DNA insert in the correct orientation.

2. Insertion of the env sequence into trp vectors

Figure 2:
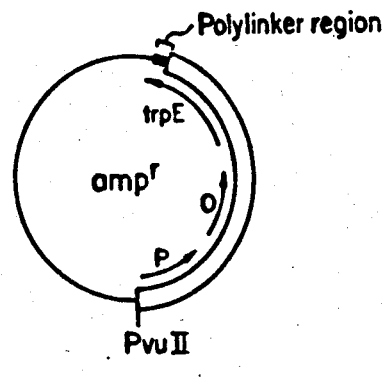
FIG. 2 illustrates the trp E expression vector pJH 11, including the polylinker sequences.

The expression vectors contained the *E. coli* trp operon promoter, operator, and trp E gene inserted into pBR322 (FIG. 2). The trp E gene was truncated at its 5'-most Bgl II site by the insertion of a polylinker sequence (Konopka et al., *J. Virol.* 51: 223 (1984)). Based on the reading frame of the restriction sites within the polylinker, one of the three possible trp vectors, pJH 11 (FIG. 2), was chosen to express the portion ENV-3 (FIG. 3). The insertion of ENV-3 into pJH11 results in the production of a fusion protein with trp E sequences at the amino-terminal end followed by ENV-3 sequences (Spindler et al., *J. Virol.* 49: 132 (1984)).

pENV-3 (assigned ATCC Accession Number 53072) was constructed by ligation of the env region between mpSW19's Bam H1 site (in the polylinker) and Hind III site (bp 7698) into Bam H1 and Hind III restricted pJH 11 (FIG. 4). *E. coli* HB101 were transformed with the ligation reaction, and the ampicillin-resistant colonies were screened by minilysates. DNA from an appropriate colony was isolated, digested with Bam H1 and Bgl II (New England Biolabs), and religated. This DNA was used to transform *E. coli* HB101. The resultant ampicillin-resistant bacteria were screened by restriction analysis for recombinant plasmids which had deleted the Bam H1 to Bgl II fragment (FIG. 4). Deletion of the fragment brought the env sequences between the Bgl II site (bp 7178) and the Hind III site (bp 7698) into the correct reading frame.

B. Protein expression

1. Transformation of *E. coli* with the trp-env construct

The recombinant trp-env expression plasmid was transferred from *E. coli* HB101 into *E. coli* C600 because the latter is a potentially better host for protein production. Transfer involved transformation of CaCl$_2$-shocked C600 with supercoiled DNA from minilysates of HB101. Bacteria were plated in the presence of ampicillin and tryptophan as described (Konopka et al., *J. Virol.* 51: 223 (1984)). Drug-resistant colonies were screened by minilysates to confirm the presence of the appropriate plasmid.

2. Expression of trp-env protein

Growth and induction of *E. coli* C600 transformed by the trp expression vector were as described (Spindler et al., *J. Virol.* 49: 132 (1984); Konopka et al., *J. Virol.* 51: 223 (1984)). Briefly, minimal medium containing tryptophan (20 μg/ml) and ampicillin (100 μg/ml) was inoculated with transformed bacteria from glycerol stocks. Cultures were grown with aeration at 37° C. overnight. The overnight cultures were then inoculated at 1:100 into fresh minimal medium containing ampicillin (100 μg/ml) but no tryptophan. These cultures were grown with aeration for 2-3 hours (up to early log phase) at 37° C. The inducer, 3-β-indoleacrylic acid (Sigma), was added to a final concentration of 20 μg/ml from freshly made stocks at 20 mg/ml in 95% ethanol.

Induced cultures were grown at 37° C. with aeration for 4 to 5 hours and then pelleted and, optionally, frozen. Protein yields from pENV-3 were between 10-30 mg/liter.

C. Isolation and purification of trp-env proteins

Fusion proteins were partially purified from cell pellets as described (Konopka et al., *J. Virol.* 51: 223 (1984)). Briefly, bacteria were resuspended in 100 ml of 50 mM Tris, pH 7.5/0.5 mM EDTA/150 mM NaCl (TNE) per liter of induced culture. Lysozyme (Sigma) was added to a final concentration of 1 mg/ml. After fifteen minutes at 0° C., NP40 was added to the mixture to a final concentration of 0.2% for ten minutes at 0° C. 1-2 mg of DNase (Sigma) was then added with 150 ml of DNase buffer (1.5M NaCl/12 mM MgCl$_2$). Reaction mixtures were incubated for one hour at 0° C. with frequent stirring. Insoluble proteins were then pelleted by centrifugation for fifteen minutes at 8000×g at 0° C. Pellets were washed two times in TNE and then analyzed for the presence of insoluble proteins by denaturing polyacrylamide gel electrophoresis. Proteins were visualized by staining with Coomassie Brilliant Blue R.

The pellet containing the insoluble material from one liter of bacteria was solubilized in 6 mls of 6M guanidinium chloride/0.1M Tris HCl, pH 7.8. To this solution was added approximately 60 mg of solid dithiothreitol (DTT), and the reduction was allowed to proceed for thirty minutes at 37° C.

The solubilized reduced protein was subjected to gel permeation chromatography on a 9.4 mm×25 cm GF-250 Zorbax column (Du Pont, Wilmington, DE). A 100 μl aliquot of the protein solution was injected onto the column and eluted with 6M guanidinium chloride at a flow rate of 0.5 ml/minute. The optical density at 280 nm was monitored, and fractions were collected at 30-second intervals. Fraction number 32, i.e., the fraction eluting between 7.75 and 8.00 mls, was used for the subsequent assays. Note: Inclusion of DTT will result in formation of insoluble metal sulfides when inferior grades of guanidinium chloride are used.

The trp-pENV3 fusion protein has also been purified as follows:

Fusion protein was partially purified from cell pellets as an insoluble pellet (described above). The pellet containing the insoluble material from four liters of bacteria was solubilized in 4 mls of 6M guanidinium chloride/0.1M Tris HCl, pH 7.8. To this solution was added approximately 100 mg of solid dithiothreitol (DTT), and the reduction was allowed to proceed for one hour at 37° C.

The solubilized, reduced protein was subjected to gel-permeation chromatography on a 2.6×87 cm column of Fractogel TSK HW-50(S) (MCB Manufacturing Chemists, Gibbstown, NJ). The 4 mls of reduced protein were pumped onto the column and eluted with $2\times10^{-4}$M DTT/$2\times10^{-3}$M ethylenediaminetetraacetic acid (EDTA)/6M guanidinium chloride (American Research Products Co., South Euclid, OH). The column was run at 0.5 mls/minute, the optical density at 280 nm was monitored, and fractions were collected at ten-minute intervals. Fractions 34 and 35, the two fractions from the center of the UV absorbing peak, were used in subsequent assays.

D. Immunological reactivity of trp-penv3 protein

1. Analysis by Western blots

Aliquots from the insoluble protein preparations expressed by pENV-3 were solubilized in 2% sodium dodecylsulphate/100 mM Tris, pH 6.8/20% glycerol/1.5M β-mercaptoethanol and electrophoresed on denaturing polyacrylamide gels. proteins were electrotransferred onto nitrocellulose (BA85, L Schleicher and Schuell, Keene, NH) and the filters blocked with 5% bovine serum albumin (Sigma). Filters were then probed with *E. coli*-adsorbed human sera pooled from AIDS patients. The filters were developed with HRP-conjugated goat αHuIg. The pool was reactive with the trp-pENV-3 fusion proteins but not with trp E protein alone.

2. Analysis by ELISA

Insoluble protein preparations expressed by pENV-3 were solubilized in 3M guanidinium chloride. Insoluble material was removed by centrifugation at 15,000×g for five minutes. Solubilized protein concentrations were determined by the method of Bradford (*Analytical Biochemistry* 72: 248 (1976)). The proteins were diluted in 0.05M carbonate/bicarbonate buffer (pH 9.6) to a final concentration of 1-2 μg/ml. Fifty μl aliquots were loaded per microtiter well and incubated at 4° C. overnight. Plates were then blocked with BLOTTO (5% [w/v] nonfat dry milk/0.01% thimerosol/0.01% antifoam A in 0.01M sodium phosphate, pH 7.2/0.15M sodium chloride) for one hour at 37° C. Pooled seropositive sera, sera from male homosexuals or LAS patients, and sera from healthy heterosexuals were diluted 1:100 with a 1:1 mixture of BLOTTO and PBS (0.01M sodium phosphate, pH 7.3/0.15M NaCl), and 50 μl of diluted serum was added per well for one hour at 37° C. The sera were removed, and the plates were washed three times in wash buffer (0.15M NaCl/0.05% [w/v] Tween 20) before adding 100 μl of the goat anti-human IgG/horseradish peroxidase conjugate (diluted 1:10,000 in 50 mM NaCitrate/0.05% Tween 20/1% heat-inactivated normal goat serum; obtained from Antibodies, Inc., Davis, CA) for one hour at 37° C. The conjugate was removed and the plates washed three times with 0.15M NaCl/0.05% (w/v) Tween 20. The ELISA assay was developed by adding 100 μl/well of substrate solution (10 mg o-phenylenediamine in 50 ml 0.05M sodium citrate, pH 7.0) for thirty minutes at room temperature. Reactions were stopped with 100 μl/well of 3N $H_2SO_4$ and the optical density at 490 nm determined by an automated ELISA reader. Protein produced by pENV-3 was found to be highly and consistently reactive with known seropositive sera.

Further screening of the pENV-3 encoded protein was carried out using material from the guanidinium chloride-solubilized pellets described above against a panel of thirty-one human serum samples. The panel included eight sera from healthy heterosexuals (defined as negative in a whole virus ELISA), two serum pools from AIDS patients, and twenty-one sera from individuals diagnosed as LAS. Sera from LAS individuals were confirmed as seropositive in a whole virus ELISA. Twelve were further confirmed by Western blot analysis. The results are shown in Table 1. These results demonstrate that sera from AIDS or LAS patients were more reactive with pENV-3 encoded protein than were sera from normal individuals. This delineation indicates that the trp-env fusion proteins can be used to screen for the presence of sera reactive with the AIDS causative virus, LAV.

3. Fluorescence slide test for detection of serum antibody to LAV

Soluble protein produced as described above is conjugated to latex beads, and the protein/bead preparation is ethanol fixed onto microscope slides. An aliquot of patient serum is incubated with the protein/beads on a slide. The slides are washed, and FITC-labeled anti-human immunoglobulin in Evans blue counterstain is added. The slides are washed, and mounting medium and coverslip applied to each.

Alternatively, the protein/bead preparation is placed in test tubes for incubation with patient serum. The tubes are centrifuged and washed, and FITC-labeled anti-human immunoglobulin in Evans blue counterstain is added. The tubes are centrifuged and the supernatant aspirated. An aliquot of the beads is placed on a microscope slide and ethanol fixed, and coverslips are mounted.

All slides are examined by fluorescence microscopy. If test serum is antibody positive, beads appear as fluorescent green spheres; if test serum is antibody negative, beads appear as red spheres.

TABLE 1
COMPARISON OF pENV-3 WITH A WHOLE VIRUS LYSATE IN AN ELISA ASSAY FOR THE DETECTION OF ANTIBODIES TO LAV

| Serum No. | Diagnosis | ELISA Whole Virus Lysate[1] | ENV-3 | Confirmed as Seropositive[2] |
|---|---|---|---|---|
| 501 | Positive control pool | 1.109 | 0.744 | yes |
| Y-1 CDC | Positive control pool | 2.000 | 0.854 | yes |
| 120 | LAS[3] and/or homosexual | 1.540 | 1.086 | yes |
| 121 | LAS and/or homosexual | 1.483 | 1.083 | yes |
| 122 | LAS and/or homosexual | 1.283 | 0.752 | yes |
| 124 | LAS and/or homosexual | 1.189 | 1.158 | yes |
| 125 | LAS and/or homosexual | 1.232 | 1.255 | yes |
| 126 | LAS and/or homosexual | 1.233 | 1.689 | yes |
| 127 | LAS and/or homosexual | 1.046 | 0.899 | yes |
| 128 | LAS and/or homosexual | 1.284 | 0.746 | yes |
| 129 | LAS and/or homosexual | 1.081 | 0.484 | yes |
| 130 | LAS and/or homosexual | 0.912 | 1.000 | yes |
| 131 | LAS and/or homosexual | 1.220 | 0.794 | yes |
| 132 | LAS and/or homosexual | 1.237 | 0.735 | yes |
| 133 | LAS and/or homosexual | 1.250 | 0.881 | yes |
| 134 | LAS and/or homosexual | 1.150 | 0.800 | yes |
| 135 | LAS and/or homosexual | 1.310 | 0.516 | yes |
| 138 | LAS and/or homosexual | 1.302 | 0.730 | yes |
| 153 | LAS and/or considered | 2.000 | 0.830 | yes |
| 154 | LAS and/or homosexual | 1.41 | 0.662 | yes |
| 155 | LAS and/or homosexual | 1.069 | 1.199 | yes |
| 157 | LAS and/or homosexual | 1.349 | 1.098 | yes |
| 666 | Unknown | 2.000 | 1.172 | yes |
| 633 | Healthy heterosexual | 0.222 | 0.113 | not seropositive |
| 637 | Healthy heterosexual | 0.097 | 0.065 | not seropositive |
| 639 | Healthy heterosexual | 0.123 | 0.045 | not seropositive |
| 641 | Healthy heterosexual | 0.199 | 0.075 | not seropositive |
| 667 | Healthy heterosexual | 0.095 | 0.113 | n.d. |
| 1890 | Healthy heterosexual | n.d. | 0.082 | n.d. |
| 1891 | Healthy heterosexual | n.d. | 0.086 | n.d. |
| 1892 | Healthy heterosexual | n.d. | 0.045 | n.d. |

[1] Prepared as described in copending patent application U.S.S.N. 558,109, filed December 5, 1983.
[2] Radiolabeled LAV antigens were disrupted in RIPA buffer (Gilead et al., Nature 264: 263 (1976)) and then were reacted with human serum. The resultant immune complexes were separated by binding to a *Staphylococcus aureus* adsorbent (Kessler, J. Immunology 115: 1617 (1975)) followed by multiple washings. Immunoprecipitated antigens were analyzed by SDS polyacrylamide gel electrophoresis (Laemmli, Nature 227: 680 (1970)) followed by fluorography. Presence of either a p25 or gp43 band was considered necessary and sufficient to confirm a sample as seropositive.
[3] LAS = lymphadenopathy syndrome
[4] n.d. = not done From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A protein which comprises a portion of the LAV envelope protein comprising the amino acid sequence of FIG. 5, starting with isoleucine, number 1, and ending with threonine, number 173, which protein is immunologically reactive with antibodies of LAV.

2. A method for determining the presence of antibodies of LAV in a biological fluid, comprising:
incubating the biological fluid with a protein produced by bacterial cells transformed with a recombinant plasmid capable of replication in bacterial host cells, said plasmid including procaryotic transcriptional and translational signals for expression, followed by a DNA sequence coding for a portion of the LAV envelope protein comprising the amino acid sequence of FIG. 5, starting with isoleucine, number 1, and ending with threonine, number 173, said protein being immunologically reactive with antibodies to LAV, thereby forming a reaction mixture; and
detecting the presence or absence of immune complexes within the reaction mixture to determine the presence of said antibodies.

3. The method of claim 2 wherein the step of detecting comprises contacting the reaction mixture with a labeled specific binding partner for the antibody and detecting said label.

4. The method of claim 3 wherein the specific binding partner is anti-human Ig or Protein A.

5. The method of claim 3 wherein the label is one selected from the group consisting of radioisotopes, fluorophores, enzymes, luminescers, and particles.

6. A method for determining the presence of LAV antigen in a biological fluid, comprising:
(a) incubating the biological fluid with a labeled protein produced by bacterial cells transformed with a recombinant plasmid capable of replication in bacterial host cells, said plasmid including proacryotic transcriptional and translational signals for expression, followed by a DNA sequence coding for a protein comprising a portion of the LAV envelope protein comprising the amino acid sequence of FIG. 5, starting with isoleucine, number 1, and ending with threonine, number 173, said protein being immunologically reactive with antibodies to LAV, and either sequentially or simultaneously, with an antibody to said protein such that specific binding occurs, thereby forming a reaction mixture; and
(b) detecting the amount of label associated with the antibody within the reaction mixture formed in step (a).

7. The method of claim 6 wherein said label is one selected from the group consisting of radioisotopes, fluorophores, enzymes, luminescers, and particles.

8. A method for producing antibodies to LAV, comprising immunizing an animal with a protein produced by bacterial cells transformed with a recombinant plasmid capable of replication in bacterial host cells, said plasmid including procaryotic transcriptional and translational signals for expression, followed by DNA sequence coding for a protein which comprises a portion of the LAV envelope protein comprising the amino acid sequence of FIG. 5, starting with isoleucine, number 1, and ending with threonine, number 173, said protein being immunologically reactive with antibodies to LAV.

9. A method for determining the presence of antibodies to LAV in a biological fluid, comprising:
   (a) incubating the biological fluid with a protein produced by bacterial cells transformed with a recombinant plasmid capable of replication in bacterial host cells, said plasmid including procaryotic transcriptional and translational signals for expression, followed by a DNA sequence coding for a protein comprising a portion of the LAV envelope protein comprising the amino acid sequence of FIG. 5, starting with isoleucine, number 1, and ending with threonine, number 173, said protein being immunologically reactive with antibodies to LAV, said bacterially produced protein being in immobilized form, and, either sequentially or simultaneously, with a labeled, monoclonal antibody to said protein such that specific binding occurs, thereby forming a reaction mixture; and
   (b) detecting the amount of label associated with the immobilized protein within the reaction mixture formed in step (a).

10. The method of claim 9 wherein the label is selected from the group consisting of radioisotopes, fluorophores, enzymes, luminescers, and particles.

11. A method for determining the presence of antibodies to LAV in a biological fluid, comprising:
    conjugating latex beads to a protein produced by bacterial cells transformed with a recombinant plasmid capable of replication in bacterial host cells, said plasmid including procaryotic transcriptional and translational signals for expression, followed by a DNA sequence coding for a protein which comprises a portion of the LAV envelope protein comprising the amino acid sequence of FIG. 5, starting with isoleucine, number 1, and ending with threonine, number 173, said protein being immunologically reactive with antibodies to LAV;
    incubating the biological fluid with the bead/protein conjugate, thereby forming a reaction mixture; and
    detecting the presence of said antibodies within the reaction mixture.

12. The method of claim 11 wherein the bead/protein conjugate is fixed to a microscope slide prior to the incubation step.

13. The method of claim 11 wherein the bead/protein conjugate is placed within a test tube prior to incubation with the biological fluid.

14. The method of claim 11 wherein the step of analyzing the reaction mixture comprises contacting the reaction mixture with a labeled specific binding partner for the antibody and detecting said label.

15. The method of claim 14 wherein the specific binding partner is anti-human immunoglobulin.

16. The method of claim 14 wherein the label is a fluorophore.

17. The method of claim 16 wherein said fluorophore is fluorescein isothiocyanate.

* * * * *